United States Patent [19]

Stillian et al.

[11] Patent Number: 5,352,360
[45] Date of Patent: Oct. 4, 1994

[54] ION CHROMATOGRAPHY SYSTEM USING ELECTROCHEMICAL SUPPRESSION AND DETECTOR EFFLUENT RECYCLE

[75] Inventors: John R. Stillian, Pleasanton; Victor M. Barreto, Santa Clara; Keith A. Friedman, Santa Clara; Steven B. Rabin, Santa Clara; Mahmood Toofan, Dixon, all of Calif.

[73] Assignee: Dionex Corporation, Sunnyvale, Calif.

[21] Appl. No.: 86,560

[22] Filed: Jul. 1, 1993

Related U.S. Application Data

[60] Division of Ser. No. 968,246, Oct. 29, 1992, Pat. No. 5,248,426, which is a continuation of Ser. No. 833,334, Feb. 10, 1992, abandoned.

[51] Int. Cl.$^5$ .................................................. B01D 15/08
[52] U.S. Cl. ................................. 210/198.2; 210/96.1; 210/243; 210/257.2; 210/259; 204/301
[58] Field of Search ............... 210/635, 638, 656, 659, 210/662, 663, 746, 96.1, 198.2, 257.2, 259, 266, 243; 204/182.4, 301

[56] References Cited

U.S. PATENT DOCUMENTS

| | | | |
|---|---|---|---|
| 3,722,181 | 3/1973 | Kirkland | 210/198.2 |
| 3,795,313 | 3/1974 | Kirkland | 210/198.2 |
| 3,897,213 | 7/1975 | Stevens | 23/253 R |
| 3,920,397 | 11/1975 | Small | 23/230 R |
| 3,925,019 | 12/1975 | Small | 23/230 R |
| 3,926,559 | 12/1985 | Stevens | 23/230 R |
| 4,242,097 | 12/1980 | Rich | 210/662 |
| 4,265,634 | 5/1981 | Pohl | 23/230 R |
| 4,314,823 | 2/1982 | Rich | 210/662 |
| 4,403,039 | 9/1983 | Ban | 436/150 |
| 4,459,357 | 7/1984 | Jansen | 436/161 |
| 4,474,664 | 10/1984 | Stevens | 210/656 |
| 4,486,312 | 12/1984 | Slingsby | 210/656 |
| 4,751,004 | 6/1988 | Stevens | 210/659 |
| 4,999,098 | 3/1991 | Pohl | 204/301 |
| 5,045,204 | 9/1991 | Dasgupta | 210/635 |

*Primary Examiner*—Ernest G. Therkorn
*Attorney, Agent, or Firm*—Flehr, Hohbach, Test, Albritton & Herbert

[57] ABSTRACT

A method of streamlining and lowering the cost of operation of ion chromatography as well as improving detection limits is disclosed. The apparatus includes chromatographic separating means through which a sample is eluted in an eluent solution including an electrolyte. The apparatus includes suppressor means having a chromatography effluent compartment means separated from a detector effluent compartment means by an ion exchange membrane, forming a chromatography effluent flow channel and a detector effluent channel, respectively. Electrode means are disposed in communication with both flow channels for passing an electric current transverse to the solution that is passing through them. The chromatography effluent flows through the chromatography effluent flow channel of the suppressor and through detector means which detects resolved ionic species therein. The effluent from the detector means is then recycled through the detector effluent flow channel and forms a sump for electrolyte ions passing across the chromatography effluent as well as supplying the water for the electrolysis reaction generating acid (or base) for suppression.

8 Claims, 5 Drawing Sheets

FIG._1

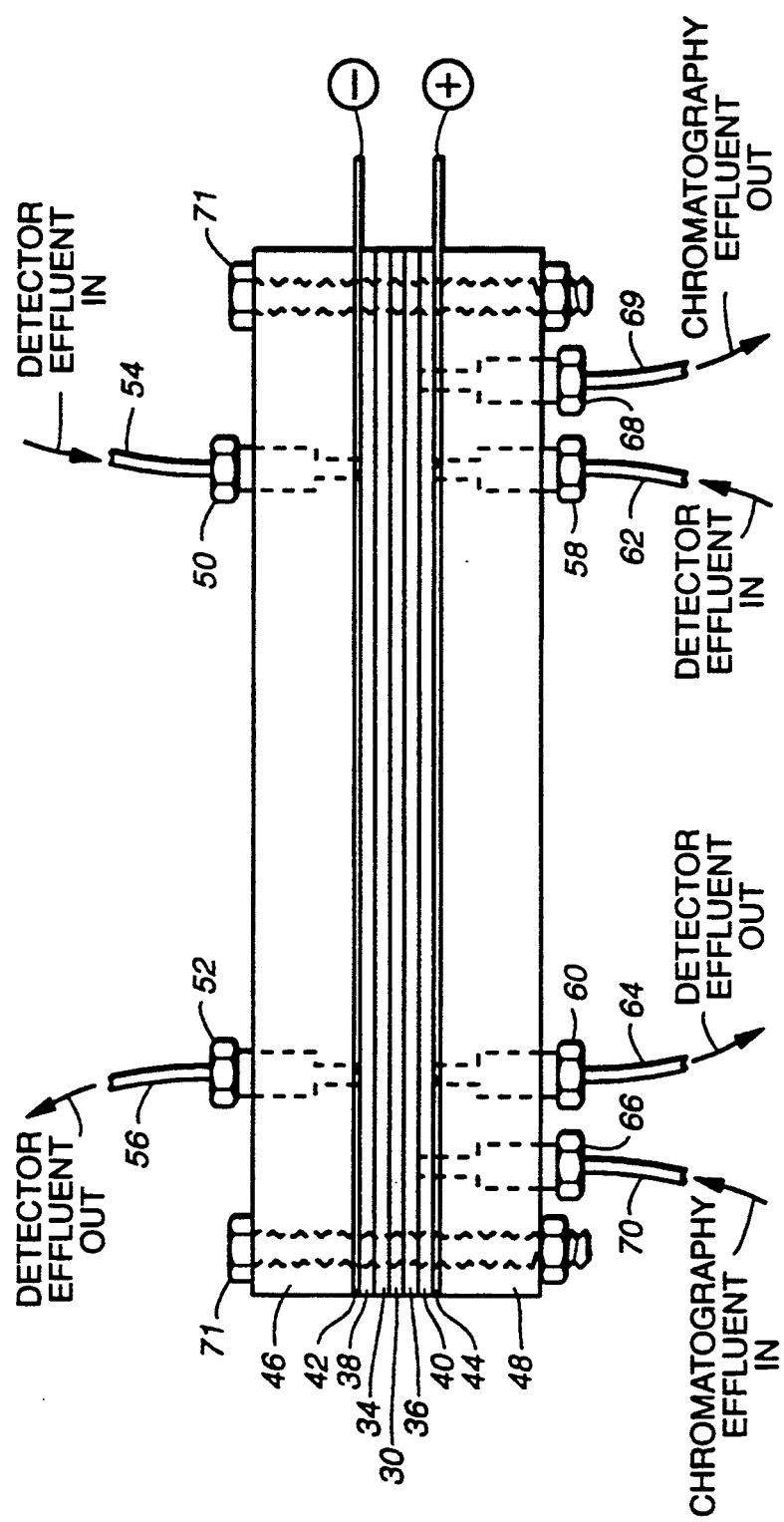
FIG._3

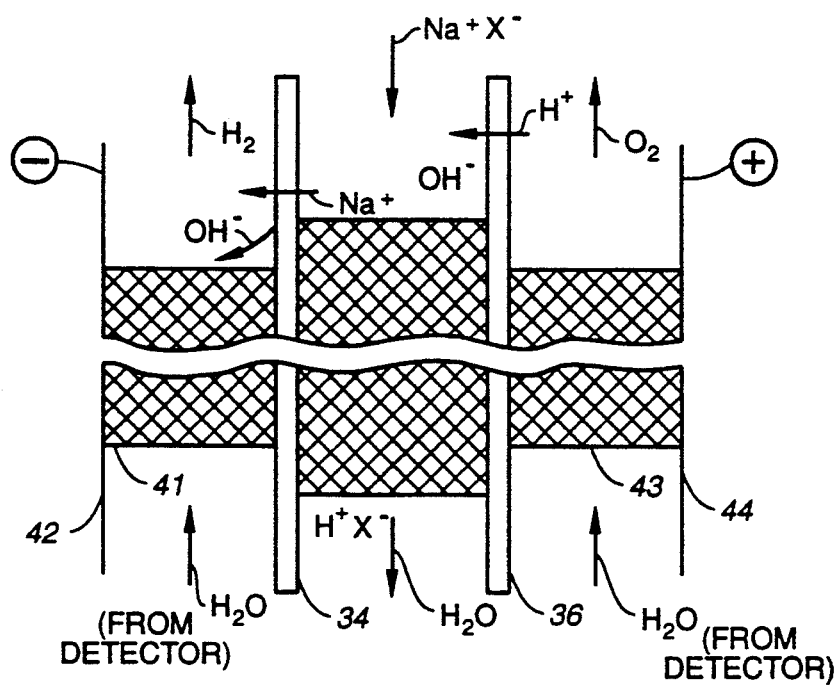
FIG._4
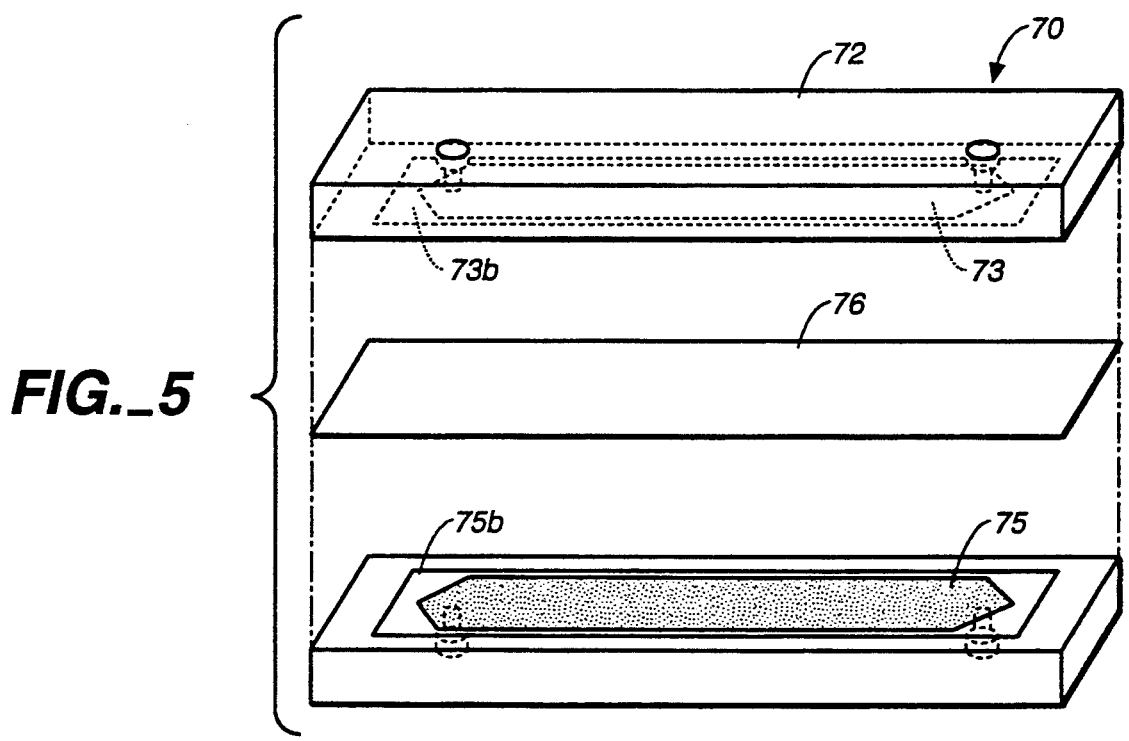
FIG._5

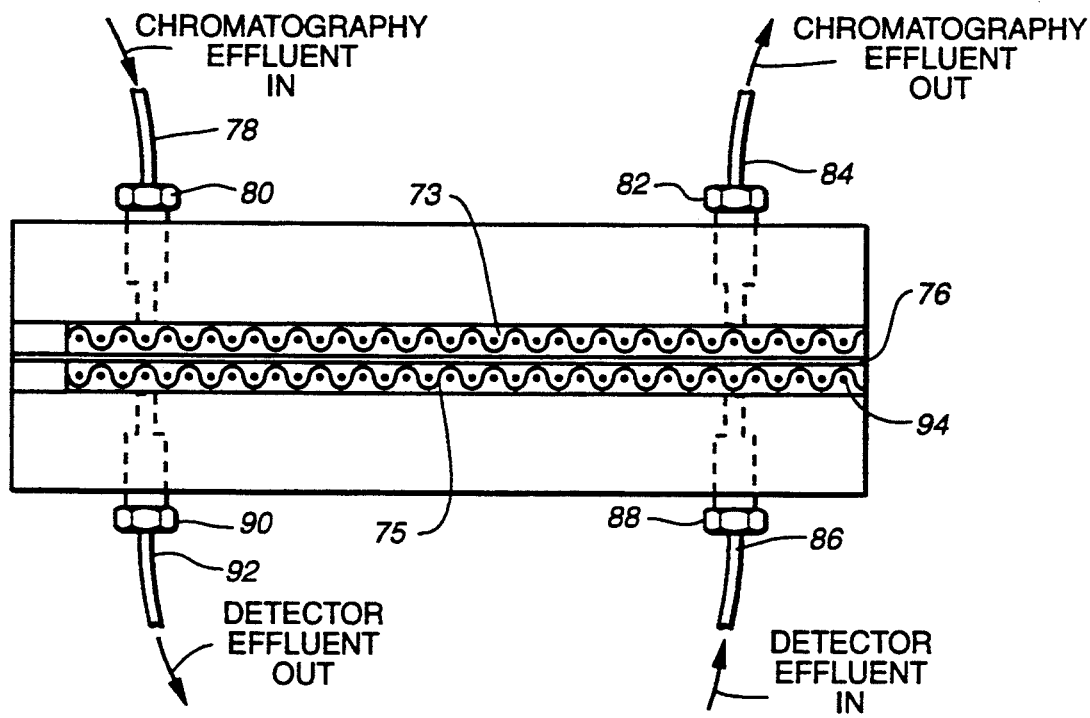
FIG._6
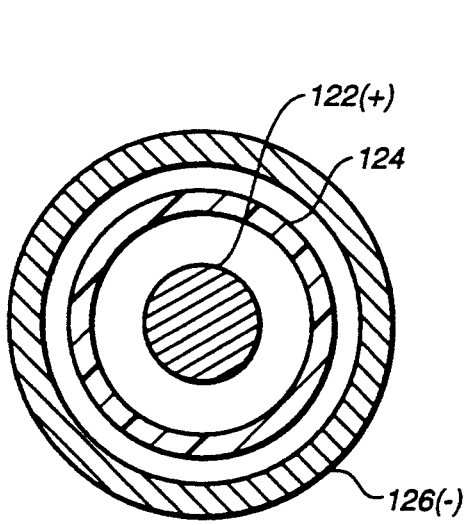
FIG._7
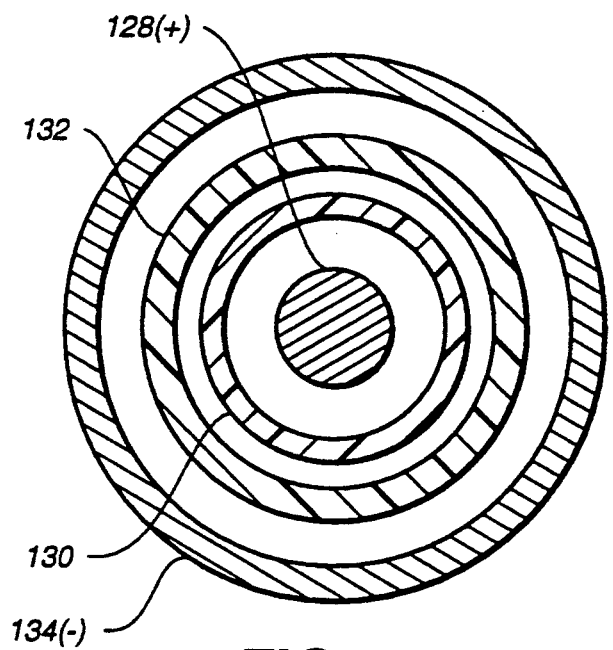
FIG._8

ION CHROMATOGRAPHY SYSTEM USING ELECTROCHEMICAL SUPPRESSION AND DETECTOR EFFLUENT RECYCLE

This is a division of Ser. No. 07/968,246, filed Oct. 29, 1992, now U.S. Pat. No. 5,248,426, which, in turn, is a continuation of Ser. No. 07/833,334, filed Feb. 10, 1992, now abandoned.

BACKGROUND OF THE INVENTION

The present invention relates to method and apparatus using electrochemical suppression of eluents for the analysis of anions or cations in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,926,559.

Suppression or stripping of the electrolyte is described in the above prior art references by an ion exchange resin bed. A different form of suppressor column is described and published in U.S. Pat No. 4,474,664, in which a charged ion exchange membrane in the form of a fiber or sheet is used in place of the resin bed. The sample and eluent are passed on one side of the membrane with a flowing regenerant on the other side, the membrane partitioning the regenerant from the effluent of chromatographic separation. The membrane passes ions of the same charge as the exchangeable ions of the membrane to convert the electrolyte of the eluent to weakly ionized form, followed by detection of the ions.

Another membrane suppressor device is disclosed in U.S. Pat. No. 4,751,004. There, a hollow fiber suppressor is packed with polymer beads to reduce band spreading. There is a suggestion that such packing may be used with other membrane forms. Furthermore, there is a suggestion that the function of the fiber suppressor is improved by using ion exchange packing beads. No theory is set forth as to why such particles would function in an improved manner.

Another suppression system is disclosed in U.S. Pat. No. 4,459,357. There, the effluent from a chromatographic column is passed through an open flow channel defined by flat membranes on both sides of the channel. On the opposite sides of both membranes are open channels through which regenerant solution is passed. As with the fiber suppressor, the flat membranes pass ions of the same charge as the exchangeable ions of the membranae. An electric field is passed between electrodes on opposite sides of the effluent channel to increase the mobility of the ion exchange. One problem with this electrodialytic membrane suppressor system is that very high voltages (50–500 volts DC) are required. As the liquid stream becomes deionized, electrical resistance increases, resulting in substantial heat production. Such heat is detrimental to effective detection because it greatly increases noise and decreases sensitivity.

In U.S. Pat. No. 4,403,039, another form of electrodialytic suppressor is disclosed in which the ion exchange membranes are in the form of concentric tubes. One of the electrodes is at the center of the innermost tube. One problem with this form of suppressor is limited exchange capacity. Although the electrical field enhances ion mobility, the device is still dependent on diffusion of ions in the bulk solution to the membrane.

Another form of suppressor is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the possibility of using water to replace the regenerant solution in the electrodialytic mode.

All of the above systems of suppression require a separate source of a flowing solution (regenerant solution or water) for a regenerant flow channel adjacent the membrane. Such systems typically require a separate regenerant reservoir and pump. It would be beneficial to eliminate the expense of such equipment and the operating expense of continuously supplying of reagent.

U.S. Pat. No. 5,045,204 discloses an electrodialytic device using an ion exchange membrane separating two flowing solutions in flow-through channels for generating a high purity chromatography eluent (e.g., NaOH). Water is electrolyzed in a product channel to provide the source of hydroxide ion for sodium which diffuses across the membrane. The patent discloses a mode of eliminating hydrogen gas generated in the product channel.

SUMMARY OF THE INVENTION

In accordance with the invention, apparatus and methods are provided for streamlining and lowering the cost of operation of ion chromatography as well as improving the system detection limits. The apparatus includes chromatographic separating means, typically a chromatography column filled with ion-exchange resin, through which a sample is eluted in an eluent solution including an electrolyte. The apparatus includes suppressor means having a chromatography effluent compartment means separated from a detector effluent compartment means by an ion exchange membrane, forming a chromatography effluent flow channel and a detector effluent flow channel, respectively. Electrode means are disposed in communication with both flow channels for passing an electric current transverse to the solution that is passing through them. The chromatography effluent flows through the chromatography effluent flow channel of the suppressor and through detector means which detects resolved ionic species therein. The effluent from the detector means is then recycled through the detector effluent flow channel and forms a sump for electrolyte ions passing across the membrane from the chromatography effluent as well as supplying the water for the electrolysis reaction generating acid (or base) for suppression.

In one preferred embodiment, flow-through ion exchange means (e.g., an ion exchange screen) is disposed in one or both flow channels, having ion exchange sites with exchangeable ions of the same charge as the ion exchange membrane. In this embodiment, the membrane is preferably in the form of a flat sheet.

In a specific preferred embodiment, the suppressor means is in sandwich form, including a second ion exchange membrane of the same charge as the first one defining therebetween the chromatography effluent flow channel. A second detector effluent compartment means is disposed to the opposite side of the second ion exchange membrane defining a second detector effluent flow channel. Ion exchange means are disposed in all flow channels. The electrode means includes oppositely charged electrodes in the two detector effluent flow channels. In one channel, the water is electrolyzed to hydronium ion for the suppression neutralization reaction in the effluent flow channel. In the other channel, water is electrolyzed to form hydroxide ions and provides a sink for electrolyte ions.

In operation, the ionic species of the samples pass through the chromatography effluent flow channel to the detector, being repelled by the ion exchange membrane. In contrast, the electrolyte in the solution passes across the ion exchange membrane under the influence of the electrical charge. For example, in the analysis of anions, the sodium ion from a sodium hydroxide eluent passes across the membrane, attracted by the cathode in the detector effluent flow channel. The solution flowing in that channel is the recycled solution from the detector and water in that stream is electrolyzed to $OH^-$ and the resulting NaOH is carried to waste. Hydronium ions generated in the second detector effluent flow channel, containing the anode, pass across the ion exchange membrane to the chromatography effluent flow channel, where they combine with hydroxide ions from the eluent to form water. It is advantageous to use the detector effluent as the sole source of the solution flowing through the detector effluent flow channel, thereby eliminating the need for a regenerant solution reservoir and its accompanying hardware.

BRIEF DESCRIPTION OF THE DRAWINGS

FIG. 3 is a side view of a membrane suppressor illustrating chromatography effluent and detector effluent flow channels in dotted lines.

FIG. 4 is a schematic expanded view of the membranes and screens showing simplified ion transfer in an electrochemical suppressor.

FIGS. 5 and 6 are an exploded view and an assembled cross-section view, respectively, of a suppressor device illustrating a single detector effluent flow channel.

FIGS. 7 and 8 are schematic cross-sectional views of two different tubular forms of electrodialytic suppressors.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids such as industrial chemical wastes, body fluids, beverages such as fruits and wines and drinking water. When the term "ionic species" is used herein, it includes species in ionic form and components of molecules which are ionizable under the conditions of the present system.

The purpose of the suppressor stage is to reduce the conductivity and noise of the analysis stream background while enhancing the conductivity of the analytes (i.e., increasing the signal/noise ratio), while maintaining chromatographic efficiency. Thus, the following parameters bear upon the performance of the suppressor: (1) dynamic capacity of suppression, measured as $\mu Eq./min$ of eluent for each device; and (2) background conductivity measured as $\mu S/cm$ per device.

Figure 1:
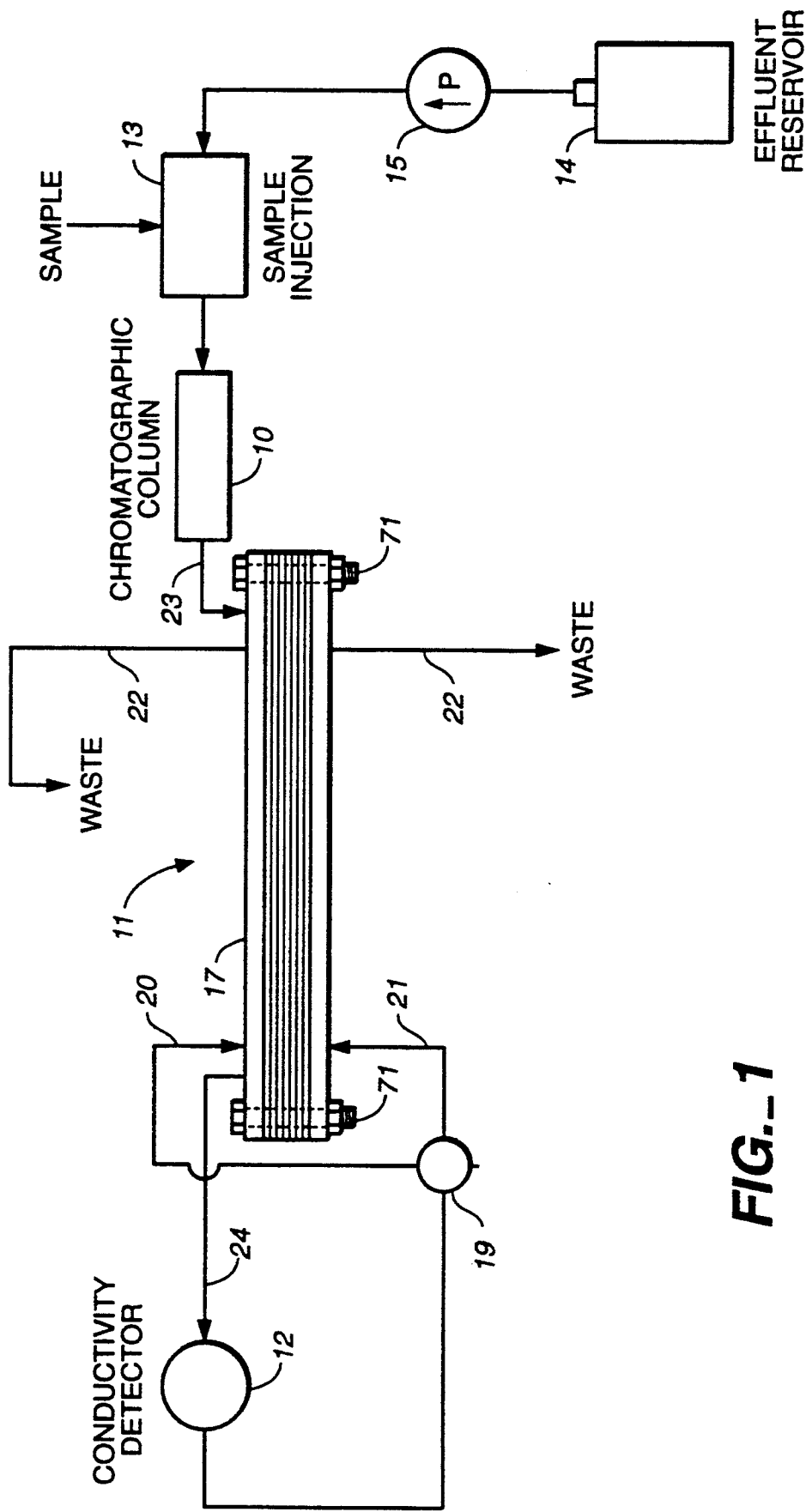
FIG. 1 is a schematic view of apparatus for performing chromatography utilizing the recycled detector effluent for the suppressor.

Referring to FIG. 1, a simplified apparatus for performing the present invention is illustrated. The system includes chromatographic separation means, typically in the form of a chromatographic column 10 which is packed with a chromatographic separation medium. In one embodiment referred to above, such medium is in the form of ion-exchange resin. In another embodiment, the separation medium is a porous hydrophobic chromatographic resin with essentially no permanently attached ion-exchange sites. This other system is used for mobile phase ion chromatography (MPIC) as described in U.S. Pat. No. 4,265,634. An ion exchange site-forming compound, including hydrophobic portion and an ion-exchange site, is passed through the column and is reversibly adsorbed to the resin to create ion-exchange sites.

Arranged in series with column 10 is suppressor means 11 serving to suppress the conductivity of the electrolyte of the eluent from column 10 but not the conductivity of the separated ions. The conductivity of the separated ions is usually enhanced in the suppression process.

The effluent from suppressor means 11 is directed to a detector, preferably in the form of flow-through conductivity cell 12, for detecting all the resolved ionic species therefrom. A suitable sample is supplied through sample injection valve 13 which is passed through the apparatus in the solution of eluent from eluent source or reservoir 14 drawn by pump 15, and then pass through the sample injection valve 13. The chromatography effluent solution leaving column 10 is directed to suppressor means 11 wherein the electrolyte is converted to a weakly conducting form. The chromatography effluent with separated ionic species is then treated by suppressor means 11 and pass through conductivity cell 12.

In conductivity cell 12, the presence of ionic species produces an electrical signal proportional to the amount of ionic material. Such signal is typically directed from the cell 12 to a conductivity meter, not shown, thus permitting detection of the concentration of separated ionic species.

The effluent from conductivity cell 12, referred to herein as the detector effluent, is directed to at least one flow-through detector effluent channel in ion-exchange membrane device 17. The membrane device will be described in detail hereinafter. The detector effluent flows through a splitter valve or tee 19 which separates the detector effluent into two different conduits 20 and 21 to supply the detector effluent to the detector effluent flow-through passages of the suppressor and then to waste through conduit 22. Alternatively, the detector effluent flows through the detector effluent chambers sequentially then to waste. The chromatography effluent flows from chromatographic column 10 to membrane device 17 through conduit 23, and from the membrane device to the conductivity detector through conduit 24.

SANDWICH SUPPRESSOR DEVICE

Referring to FIGS. 2–5, a device is illustrated in the form of a sandwich suppressor device including a central chromatography effluent flow channel defined on both sides by ion-exchange membranes to the exterior of which are two detector effluent flow channels.

Figure 2:
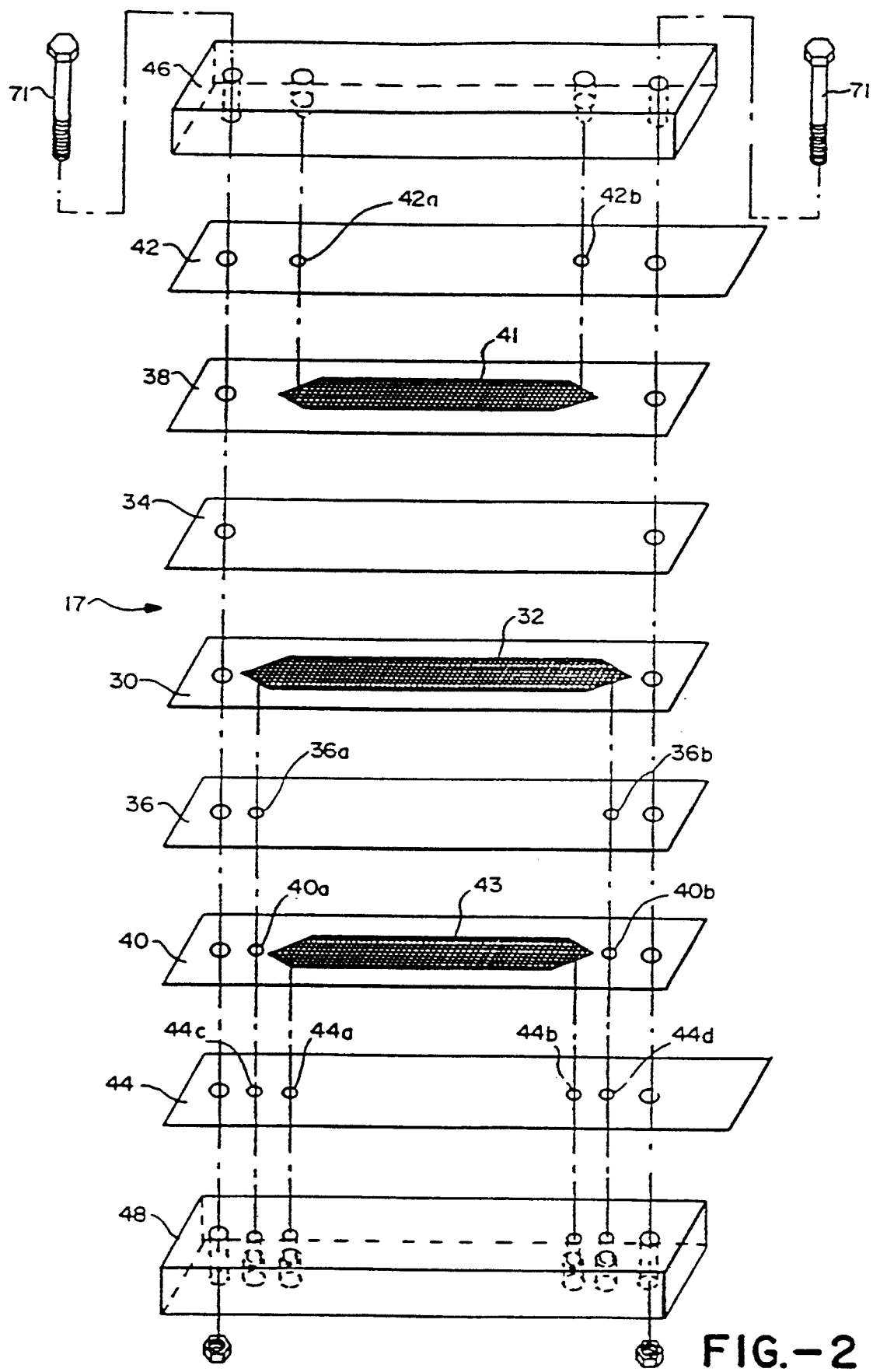
FIG. 2 is an exploded view of a sandwich suppressor device useful in the present invention.

Referring specifically to FIGS. 2 and 3, membrane device 17 is illustrated which includes a central chromatography effluent flow channel flanked by detector effluent flow channels. Membrane device 17 includes means defining a chromatography effluent flow channel in the form of a chromatography effluent compartment, partially bounded by chromatography effluent gasket 30 defining a central cavity. To minimize dead space in the cavity it is preferable to form both ends of the flow channels in a peak or V-shape. Flow-through ion-exchange means, preferably bridging means in the form of chromatography effluent screen 32, is disposed in the cavity. Membrane sheets 34 and 36 are mounted to extend along opposite sides of chromatography effluent screen 32 and, together with gasket 30, define the outer perimeter of the chromatography effluent flow channel. Openings 36a and 36b are provided for effluent inlet and outlet to the effluent flow channel.

Detector effluent gaskets 38 and 40 are mounted to the facing surfaces of membrane sheets 34 and 36, respectively and define detector effluent flow channels. Bridging means may be provided in the detector effluent flow channels in the form of screens 41 and 43, respectively. Openings 40a and 40b are provided for inlet and outlet detector effluent flow through gasket 40. To simplify connections with the external flow lines, it is preferable to form the chromatography effluent flow channel slightly longer than the flanking regenerant flow channels.

As illustrated, spaced electrode means in the form of flat plate electrodes 42 and 44, are placed on the exterior sides of gaskets 38 and 40, respectively, extending substantially across the length and width of the chambers in the gaskets. An electrical potential is applied across the electrode means. Electrode 42 includes openings 42a and 42b to permit the inlet and outlet flow of detector effluent solution to the detector effluent flow channel in gasket 38. Similarly, electrode 44 includes inlet and outlet openings 44a and 44b, respectively, for detector effluent liquid flow and to the detector effluent flow channel and gasket 40, and also defines inlet and outlet openings 44c and 44d for the chromatography effluent flow channel defined by gasket 30.

External support blocks 46 and 48 are formed of a rigid nonconductive material, such as polymethylmethacrylate, or polyether-ether ketone (PEEK) and serves to provide structural support for the remainder of membrane device 17. Referring to FIG. 3, fittings 50 and 52 are provided for detector effluent inlet and outlet lines 54 and 56, respectively. Similarly, fittings 58 and 60 are provided for detector effluent inlet and outlet lines 62 and 64, respectively. Fittings 66 and 68 are provided for chromatography effluent inlet and outlet lines 70 and 69, respectively. The fittings may be mounted to the support blocks by any conventional means such as mating screw threads.

The above assembled sheets and gaskets are mounted under pressure supplied by bolts 71 to form liquid-tight seals. Also, by use of such pressure in combination with appropriate sizing of the screen (or other bridging means described below) in comparison to the flow channel dimensions, the screen extends substantially the entire distance across the flow channels and contacts the membranes, resulting in significantly improved ion transport and efficiency. It is preferable for maximum membrane transfer efficiency to connect the lines to the chromatography effluent and detector effluent flow channels for countercurrent flow.

Detector effluent gasket 30 may be formed of any suitable material which provides a liquid seal for the chromatography effluent flow channel which it defines. A suitable material for the gasket is a flexible liquid silicone-based rubber such as supplied under the name RTV by General Electric Co. or a plastic sheet such as "Parafilm" supplied by American Can Co. A similar material may be used for detector effluent gaskets 38 and 40.

Ion-exchange membrane sheets 34 and 36 may be of a type such as disclosed in U.S. Pat. No. 4,486,312. In particular, such sheets may be cation-exchange or anion-exchange membranes with polyethylene, polypropylene, polyethylene-vinylacetate-based substrates. Other suitable substrates include poly-vinylchloride or polyfluorocarbon-based materials. The substrate polymer is solvent and acid or base resistant. Such substrates are first grafted with suitable monomer for later functionalizing. Applicable monomers include styrene and alkylstyrenes such as 4-methylstyrene, vinylbenzylchloride or vinylsulfonates, vinylpyridine and alyklvinylpyridines. As an example, to form a cation-exchange membrane, the sheets grafted with styrene monomers are functionalized suitably with chlorosulfonic acid, sulfuric acid, or other $SO_2$ or $SO_3$ sources. To forman anion-exchange membrane, the sheets grafted with vinylbenzylchloride monomers are functionalized with alkyl tertiary amines such as trimethylamine or tertiary alkanolamines, such as dimethylethanolamine. Particularly effective membranes are no more than 10 mil thick, and preferably no more than 2–4 mil when wet. Suitable polyethylene substrate membranes of the foregoing type are provided by RAI Research Corp., Hauppauge, N.Y. (the cation exchange membrane provided under designation R5010 (0.008 in. thick) and the anion-exchange membrane under designation R4015 (0.004 in. thick)). Other cation exchange membranes supplied by the same company which are fluorocarbon based include R1010 (0.002 inch thick) and R4010 (0.004 inch thick).

Chromatography effluent screen 32 may be formed integral with chromatography effluent gasket 30 or may be inserted independently into the effluent flow channel. A screen integral with the surrounding gasket material may be formed by cutting a gasket from plastic sheet to include the desired flow path and pressing this gasket into a rectangular piece of screen such that only the flow path is not covered by the gasketing material.

Detector effluent screens 41 and 43 may be formed in the same manner as set forth with respect to chromatography effluent screen 32.

The flow-through ion-exchange means, preferably in the form of bridging means, includes continuous portions which extend substantially the entire distance across the chromatography effluent flow channel transverse to flow. In the embodiment of FIGS. 2 and 3, this distance extends between membrane sheets 34 and 36. In the alternate embodiment of FIG. 6 described below, only one membrane separates one regenerant flow channel from the effluent flow channel. There, the transverse distance spanned by the bridging means is from the membrane to the opposite wall defining the chromatography effluent flow channel. The bridging means defines a continuous convoluted flow-through passageway in the chromatography effluent flow channel along substantially the entire length of the membrane. This creates turbulence and thus increasing the efficiency of mixing and transfer of the ions across the membrane as described below. The physical configuration of the screen may vary so long as its bridging function and turbulence-producing function is accomplished. Thus, the screen may be provided with a weaving pattern either perpendicular or diagonal to the direction of flow. Also, the fibers may be smooth or contain protrusions such as bumps.

A major function of the flow-through ion-exchange means is to provide a site-to-site path for ions in the direction transverse to the chromatography effluent flow channel to increase the efficiency of ionic transfer across the ion-exchange membrane as more fully described below. Bridging means in the form of a screen may be functionalized for this purpose in a manner analogous to the functionalization of the ion-exchange membranes set forth above. Suitable screens may be formed of the same base polymers grafted with the same functionalizing monomers as those set out above for the membranes.

The maximum chromatographic efficiency of the screen embodiment of the flow-through ion-exchange means may be achieved using a relatively small mesh (measured after functionalization), e.g. on the order of $110\mu$ mesh size or less with relatively thin fibers, e.g., on the order of 0.004 inch in diameter. An open area in the flow channel on the order of 5% to 70% (preferably, on the order of 8%) provides excellent efficiencies. A suitable proportion of grafting monomer to grafting polymer substrate is on the order of 5%–50% (preferably about 25% to 35%). In order to obtain maximum efficiency, the effluent flow channel should be fairly narrow, e.g., on the order of 0.5 cm, with the weave pattern oriented diagonally to the direction of flow. As the exposed membrane surface area increases suppression capacity increases. However, practical limits are prescribed by known principles of chromatography. For example, to minimize band broadening, a minimum volume is desired.

To maximize the dynamic capacity, the regenerant screens may be functionalized to relatively high ion exchange capacity, e.g. 2 meq/g. Also, as with chromatographic efficiency, it is preferable to orient the fibers of the screen diagonally to the direction of flow. Parameters relevant to the screen's function are set out in U.S. Pat. No. 4,999,098, incorporated herein by reference.

In the embodiments of FIGS. 2 and 3, an electrical potential from a direct current source (not shown) is applied between electrodes 42 and 44 from any suitable source. The electrodes are formed of highly conductive material which is inert to the solutions being passed through the membrane suppressor. Platinum is a preferred form of electrode for this purpose.

In one mode of operation of the suppressor device 17, effluent from chromatographic column 10 is directed through the chromatography effluent flow channel bounded on both sides by ion-exchange membranes 34 and 36 partitioning the detector effluent from the chromatography effluent. The detector effluent flows from the conductivity cell through the detector effluent channels. The membrane is preferentially permeable to ions of the same charge as the exchangeable ions of the membrane and resists permeation of ions of opposite charge. The exchangeable ions of the membrane are in the ion form necessary to convert the developing reagent of the eluent to a weakly ionized form. For maximum capacity, the detector effluent flow is countercurrent to the effluent flow. The chromatography effluent from chromatographic column 10 is passed through the chromatography effluent flow channel and contacts both membranes. The membranes are simultaneously contacted on their outer sides with the detector effluent flowing in the opposite direction through the detector effluent flow channel so that the membrane forms a selective permeability partition between the detector effluent and the chromatography effluent. Ions extracted from the chromatography effluent at the active ion-exchange sites of the membranes are diffused through the membranes and are exchanged with ions of the detector effluent, and thus diffused ultimately into the detector effluent. Application of a potential across the electrodes increases the mobility of the ions across the membrane. The resolved ionic species in the effluent leaving the suppressor device are detected, as with a conductivity detector.

FIG. 4 schematically illustrates the electrochemical operation of the present invention for a particular system, using a sandwich suppressor with screens in the chromatography effluent and detector effluent channels, and applying an electrical potential between spaced electrodes. The system illustrated is for anion analysis and includes sodium hydroxide as the electrolyte of the effluent to be converted into weakly ionized form ($H_2O$) in the suppressor. Thereafter, the solution passes through the conductivity cell and is recycled to the detector effluent flow channel. The ion-exchange membrane sheets allow the positively charged sodium and hydronium ions to permeate across the membrane together.

A suitable ion-exchange membrane for this purpose is a sulphonated polyethylene sheet. Hydroxide ions tend not to permeate the membrane sheet because of Donnan Exclusion forces. Thus, the sodium hydroxide stream is converted to deionized water in the chromatography effluent flow channel and the sodium ions permeate the membrane sheet and are dispersed in the negatively-charged detector effluent flow channel as NaOH and thus ultimately routed to waste through the detector effluent outlet lines. Applying a potential across electrodes 42 and 44 increases the kinetics of ion flow across the membrane and thereby increases capacity and, thus, the suppression efficiency of the suppressor device.

In the illustrated embodiment, the sodium ions of the electrolyte in the chromatography effluent channel diffuse across the negatively-charged membrane into detector effluent channel under the influence of the negative electrode. The hydronium ions generated at the anode by electrolysis of water, flow from the positively-charged detector effluent flow channel adjacent the positive electrode across membrane 36 into the chromatography effluent flow channel to form water with hydroxide ions therein. The sodium ions, being attracted to the negative electrode, are more rapidly removed from the effluent channel leading to a substantial increase in the capacity of the membrane device.

In operation of the system of FIG. 4, in the positively charged detector effluent flow channel, hydronium ion is generated for passage through membrane 36 according to the following equation:

$$6H_2O \rightarrow 4H_3O^+ + O_2 + 4e^-  \quad (1)$$

In the chromatography effluent flow channel, the sodium ion passes through membrane 34 under the influence of the cathode. Hydroxide is converted to water according the following equation:

$$OH^- + H_3O^+ \rightarrow 2H_2O  \quad (2)$$

In the negatively-charged detector effluent flow channel, the sodium ion is converted to NaOH with hydroxide ion produced by the following equation:

$$4e^- + 4H_2O \rightarrow 4OH^- + 2H_2  \quad (3)$$

Screens 32, 41 and 43 substantially increase the capacity of the suppressor device to remove ions from the chromatography effluent stream. The threads of the screen preferably extend substantially across the chromatography effluent flow channel transverse to flow to contact both membranes. In the illustrated device, the chromatography effluent screen extends the distance between membranes 34 and 36.

The functionalized screens include exchangeable ions of the same charge as those of the membranes. In this manner, the screen provides a direct site-to-site contact between the membrane walls for the ions to be diffused through the membranes. It has been found that the capacity of the system is significantly increased by the use of such functionalized screen in the effluent flow channel. The capacity is still further increased by using the same types of screens in the regenerant flow channel.

Referring again to FIG. 3, the detector effluent flow channels may include neutral screens rather than functionalized screens, although this system does not have as much dynamic suppression capacity. The advantage of such unfunctionalized screens is that they provide turbulence in the detector effluent flow channel to increase the mixing efficiency. However, if desired, such screens may also be eliminated.

The potential to be applied to the electrodes in the above system may be relatively low due to the presence of the functionalized bridging means in the effluent channel. Thus, capacity is substantially improved with a voltage of about 1–20 VDC, preferably about 2–6 VDC.

While the above sandwich suppressor embodiment includes a central chromatography effluent flow channel separated by two membranes from two coextensive detector effluent flow channels, the system is also applicable to the use of a single detector effluent flow channel separated from the chromatography effluent flow channel by a single membrane.

Referring to FIGS. 5 and 6, another embodiment of suppressor means 70 is illustrated using a single regenerant flow channel. Suppressor means 70 includes upper rigid support block 72 with chromatography effluent flow channel wall 73 and lower support block 74 with detector effluent flow channel wall 75, separated by an ion-exchange membrane 76 of the type described above.

The chromatography effluent flows into the suppressor device through effluent inlet 78, fitting 80 and flows along chromatography effluent flow channel defined by wall 73, through screen 94 and then through fittings 82 and out chromatography effluent outlet line 84. Similarly, detector effluent solution flows from inlet line 86 through fittings 88 across the detector effluent flow channel defined by wall 75, out fitting 90 and through detector effluent outlet 92 to waste. The device of FIGS. 5 and 6 is used in the overall system of FIG. 1 in place of the device of FIGS. 2–5.

The liquid flows through the channels formed by the spacing among the projections. The dimensions of the projections and spacing is selected to provide the desired frequency of contacts with the flowing ions to increase their mobility across the membrane and to create sufficient turbulence for increased mixing efficiency.

Suitable eluent solutions for anion ion chromatography include alkali hydroxides, such as sodium hydroxide, alkali carbonates and bicarbonates, such as sodium carbonate, alkali borates, such as sodium borate, combinations of the above, and the eluent systems of the aforementioned patents.

The recycle system of the present invention is also applicable to the analysis of cations (e.g., lithium, sodium, ammonium, potassium, magnesium, and calcium). In this instance, the electrolyte of the eluent is typically an acid which does not damage the membrane. Methane sulfonic acid has been found to be inert to the membrane under electrolytic conditions. Other acids such as nitric acid and hydrochloric acid produce electrochemical by-products that may damage the membrane and are, thus, not generally preferred for that typical membrane.

In cation analysis, the flow of the electrolyte ion is from the cathode toward the anode, rather than the reverse as in anion analysis and the ion exchange screens and membranes are aminated and permeable to anions. Thus, in the negatively charged detector effluent flow channel, water is converted to hydroxide ion and hydrogen gas. The hydroxide ion passes through the adjacent membrane into the chromatography effluent flow channel and combines with hydrogen ion (or an amine or other basic organic molecule group) to form weakly ionized electrolyte. The negatively-charged transmembrane ion travels through the second membrane into the positively-charged detector effluent flow channel under influence of the anode to form an acid which passes to waste. In summary, for cation analysis, the electrical charges of the analyte, eluent reagent, and membranes are reversed for cation analysis and anion analysis.

In a single detector effluent flow channel, gases are generated in the chromatography effluent which can interfere with detection in the conductivity cell. For example, for ion analysis, oxygen is generated in the detector effluent flow channel. One way to remove the oxygen is to pass the effluent from the chromatography effluent flow channel through a gas diffusion removal device, using a gas diffusion membrane, prior to reaching the conductivity cell. One such device is disclosed in the U.S. Pat. No. 5,045,204. In another embodiment, a gas diffusion membrane forms a wall defining the opposite side of the chromatography effluent flow channel from the ion exchange membrane. An inert gas stream such as nitrogen, may be flowed in a channel bounded on one side by the gas diffusion membrane, preferably countercurrent to the chromatography effluent flow. In this manner, the solution leaving the chromatography effluent flow channel is degassed prior to reaching the conductivity cell. In either event, a suitable gas diffusion membrane is a gas diffusion membrane such as one sold under the trademark Accural ® or Celgard ®.

The above system illustrates an ion exchange screen as the preferred flow-through ion exchange means. However, it should be understood that other ion exchange means may also be employed for the sandwich suppressor or other relatively flat suppressor. For example, ion exchange particles may be packed in the flow channels for this purpose. Here, it would be preferable to include some mode to keep the ion exchange particles in the device by using a porous polymeric support that has smaller pores than the resin being used, such as sintered polyethylene available from General Polymeric.

Referring to FIG. 7, a schematic cross-sectional view of a tubular form of the electrodialytic suppressor of the present invention is illustrated. In this instance, it is assumed that the chromatography effluent channel is the lumen of the innermost tube. The device includes anode 122 (in the form of a rod or wire, e.g., formed of platinum, gold, carbon or stainless steel), cation exchange membrane 124, and outer wall 126, which may be formed of a conductive material to serve as the cathode. Preferably, flow-through ion exchange means in the form of ion exchange resin is disposed in the chromatographic effluent flow channel, the detector effluent flow channel or both. This system is comparable in general function to the one illustrated in FIG. 4. Alternatively, the detector effluent flow channel may be the lumen of the inner tube. In this instance, the polarities of the electrodes are reversed. Membrane 124 may be formed of stretched or unstretched tubular ion exchange membranes, e.g., Nafion 811X from Perma-Pure Products, N.J. Outer wall 126 may be formed of an 18 GA. stainless steel (SS) tubular case.

FIG. 8 illustrates a tubular type of dual-membrane suppressor of similar function to the sandwich membrane suppressor. It is generally constructed by inserting a length of suitably inert wire inner electrode 128 into a length of tubular inner membrane 130 which is itself inserted inside a length of somewhat larger diameter tubular outer membrane 132 and enclosing the whole assembly in the stainless steel tube 134 of appropriate dimensions. The outer tube itself functions as the electrode, connections being made at the ends to allow access to the flow channels between the inner electrode and inner membrane, between the two membranes (annulus) and between the outer membrane and stainless steel case.

A major advantage of the foregoing invention is that it avoids the necessity of a regenerant reservoir and associated pumping hardware. Thus, it is preferable that the sole source of solution in the detector effluent flow channel be the effluent from the detector. In that embodiment, there is a one-to-one equivalent of flow through the detector effluent flow channel and through the chromatography flow channel. If desired, in some systems, this flow rate could be increased by supplementing the solution flow through the effluent flow channel.

The power requirements for this system are dependent to some extent upon the flow rate through the system and the concentration of electrolyte solution. For this purpose, a suitable flow rate or chromatography effluent are about 0.01 to 10 mls/min. and, preferably, 0.25 to 2 mls/min. For such flow rates, suitable power requirements are 2 to 12 volts at 0.050 to 2 amps. This applies to both the flat membrane suppressor and tubular membrane assembly.

Other alternative configurations (not shown) of the suppressor can be used in accordance with the present invention. For example, referring to the suppressor of FIGS. 2-4, the positions of screens 41 and 43 may be reversed with the positions of electrodes 42 and 44, respectively. Specifically, in such alternative configurations, electrodes 42 and 44 extend along, and are pressed flush against, ion exchange membranes 34 and 36, respectively. The electrodes are in contact with the solution flowing through the outside detector effluent flow channels. In this instance, the electrodes include openings to permit ion transport across the ion exchange membranes between the outside detector effluent flow channels and the chromatograph effluent flow channels. Such openings may be formed in a number of known ways, e.g., by punching of spaced holes (typically from 0.010" to 0.250" across), or by forming the electrodes of a woven screen, or by notching an inert foil electrode so that the electrode forms a zig-zag or serpentine pattern along the length of the chamber. For example, platinum wire bent into a zig-zag pattern can be used, however, platinum or platinum plated foil is preferable to prevent excessive resistive heating.

In yet another embodiment (not shown), a "hybrid" suppressor may be formed in which the electrode and screen is in the configuration illustrated in FIGS. 2-4 for one of the outside flow channels while in the opposite outside flow channel the electrode and screen are reversed in the manner described in the previous paragraph. An effective hybrid configuration for an ion analysis is formed in which an anode with spaced openings is flush against the ion exchange membrane and the cathode (the compartment to the left of FIG. 3) is in the configuration illustrated in FIGS. 2-4. The same configuration is preferred for cation analysis.

In order to illustrate the present invention, the following examples of its practice are provided.

EXAMPLE 1

In this example, a sandwich suppressor device as illustrated in FIGS. 2-5, suitable for anion analysis, is constructed for use in the system of FIG. 1.

The cation-exchange screens 32, 41 and 43 are formed as follows. The base screen is of a polyethylene monofilament type supplied by Tetko, Inc. Such screen is immersed in a solution of 30% styrene w/w in methylene chloride solvent. Grafting occurs by irradiation with gamma rays at a dose of 10,000 rads/hour for about 48–120 hours at 80°–90° F. under nitrogen atmosphere. The screen is then soaked in w/w chlorosulfonic acid in methylene chloride for 4 hours at about 40° C. The screen is then immersed in 1M KOH at 55° C. for 30 minutes.

The substrates for the ion exchange membranes 34 and 36 are film or sheet type made of PTFE (Teflon). The substrate polymer is solvent and acid or base resistant. Such film is first grafted with styrene monomer and then functionalized to form a cation-exchange membrane. Membrane functionalization, sulfonation, is performed in the same manner as functionalizing the screens in the previous paragraph.

The gasket is formed of an inert, chemical resistant material suitable for providing a liquid seal for the flow channel it defines.

The overall hardware includes external support blocks made of a rigid nonconductive material (PEEK) serving to house the screens, membranes and electrodes. It also provided structural support for the suppressor. The top block has four fittings (one pair for the eluent inlet and eluent outlet and other pair for regenerant inlet and regenerant outlet, respectively). The blocks are pressed together by conventional means, such as screws, to obtain a liquid-tight seal.

The sub-assemblies are formed as follows. A screen with surrounding gasket material is formed by cutting a gasket from plastic film that includes the desired flow path and pressing this gasket into the screen such that only the flow path is not covered by the gasket material. For each gasket two rectangles of ultra-low molecular weight polyethylene (Parafilm "M", American National Can Company) are cut with the appropriate dimensions of the flow channel also cut out. The screen is sandwiched between the Parafilm gaskets, and the stack is pressed to 10,000–20,000 psi at ambient temperature. One eluent screen/gasket assembly and two regenerant ones made with sulfonated screen and Parafilm are required per suppressor. The screen mesh (the size of the screen opening) for the central screen 32 are 140 $\mu$m, and 410 $\mu$m for the outside screens 41 and 43.

Two rectangles of cation-exchange membrane are cut to match the inlets and outlets of the flow path profile and the overall dimension of the screens. 3 mil thick polytetrafluorethylene (Teflon) base membrane is used.

An anode and a cathode made of conductive, chemically platinum foil, 0.025 mm thick (Johnson Matthey Electronics), with measurements of 1.0 by 12.0 cm were used.

The system is in the form of a chromatographic column arranged in series with the suppressor. The solution leaving the column is directed to the suppressor wherein the electrolyte is converted to a weakly conducting form. The effluent was then directed to a detector in the form of a flow-through conductivity cell for detecting all the resolved ionic species. The effluent after passing through the conductivity cell is re directed to the inlet port of the outside channels which the detector cell effluent is electrolysed supplying hydronium ions (H+) for neutralization reaction. The electrical potential required to operate the suppressor was generated by a DC power supply unit (0–10 VDC).

A suppressor of the above type with central gasket 30 of dimension 1.0 cm wide×14.3 cm long using an aqueous solution of 100 mM NaOH as the eluent (simulating a chromatography effluent) at a flow rate of 1.0 and 2.0 mL/min gave the following results:
chromatography effluent flow rate: 1.0 mL/min
current applied: 200 mA
voltage: 3.60 V
suppressed background conductivity: 3.07 $\mu$S
chromatography effluent flow rate: 2.0 mL/min
current applied: 400 mA
voltage: 4.07 V
suppressed background conductivity: 3.20 $\mu$S

EXAMPLE 2

The suppressor of Example 1 was used with the following different parameters. A suppressor with a central gasket 30 of dimension 0.25 cm wide×14.3 cm long using 150 mM NaOH as the eluent (simulating chromatography effluent) at a flow rate of 0.25 and 0.50 mL/min gave the following results:
eluent flow rate: 0.25 mL/min
current applied: 100 mA
voltage: 3.70 V
suppressed background conductivity: 4.42 $\mu$S
eluent flow rate: 0.50 mL/min
current applied: 200 mA
voltage: 4.35 V
suppressed background conductivity: 3.88 $\mu$S

EXAMPLE 3

In this example, the system of Example 1 is used except that it was built for use in cation analysis.

An anion-exchange screen is formed as follows. A polyethylene screen of the same type as Example 1 is immersed in 30% vinylbenzylchloride w/w in methylene chloride solvent. Grafting occurs by irradiation with gamma rays of a dose of 10,000 rads/hour for about 100–200 hours at 80°–90° F. under nitrogen atmosphere. The screen is heated under reflux in a solution of 20% w/w trimethylamine in methylene chloride for 24–56 hours.

The substrate for the membrane is film or sheet-type made of PTFE (Teflon). The substrate polymer is solvent and acid or base resistant. Such film is first grafted with vinylbenzylchloride monomer and then functionalized to form an anion-exchange membrane. The functionalization, amination, of the membrane, is done by heating under reflux in a solution of 20% trimethylamine w/w in methylene chloride for 24–56 hours.

The gaskets, electrodes, hardware are subassemblies substantially the same as in FIG. 1.

A suppressor with an eluent gasket of dimension 0.7 cm wide×14.3 cm long using 50 mM methane sulfonic acid (MSA) as the eluent at a flow rate of 1.0 mL/min gave the following results:
eluent flow rate: 1.0 mL/min
current applied: 200 mA
voltage: 4.5 V
suppressed background conductivity: 0.58 $\mu$S

EXAMPLE 4

The suppressor of Example 3 was used with the following differences. A suppressor with an eluent gasket of dimension 0.25 cm wide×14.3 cm long using 100 mM MSA as the eluent at a flow rate of 0.25 mL/min gave the following results:
eluent flow rate: 0.25 mL/min
current applied: 150 mA
voltage: 6.1 V
background conductivity: 1.28 $\mu$S

EXAMPLE 5

The anion analysis system of Example 1 is used except for a different form and location of the electrodes. Specifically, the electrodes are pressed flush against the outside of the membranes defining the actual flow channel. The electrodes included openings for contact with the membrane of solution in the outside passages. The solution in the outside passages flows between the electrodes and outside walls of the suppressor.

The suppressor was sized for use with 2 mm columns, and its central flow channel was 88 mm long×5 mm wide. Its two electrodes were made of platinum foil: 63 mm long×8 mm wide by 0.025 mm thick. Holes, 3 mm diameter and spaced 3.5 mm apart, were punched down the center-line of each electrode. A platinum wire was attached to each electrode for connection to the power supply. Each electrode was attached to a screen/gasket subassembly. the membrane subassemblies were made of reinforced, sulfonated cation exchange membrane 0.006" thick (selemion membrane, Asahi Glass, Japan) Selemion CMV.

This anion suppressor suppressed 0.35 ml/min of 100 mN NaOH to 6.1 $\mu$S with 62.5 mA at 3.97V.

EXAMPLE 6

In this example, the electrode arrangement of Example 5 was used for cation analysis using the components of Example 3. The system suppressed 1.0 ml/min of 20 mN methane sulfonic acid to about 1.5 $\mu$S with 100 mA at 4.3V.

EXAMPLE 7

This is a hybrid anion suppressor in which the anode with openings 0.020" across and formed by 0.004" dia. Pt. wire woven in a square weave pattern (Johnson Matthey) is flush against the adjacent membrane (as in Example 6) and the cathode is spaced from the other membrane and against the outside wall (as in Example 1). The anion suppressor suppressed 1.0 ml/min of 100 mN NaOH to 2.5 $\mu$S with 500 mA at 3.76 V.

EXAMPLE 8

The unit of Example 7 was formed as a cation suppressor. It suppressed 1.0 ml/min of 100 mN methane sulfonic acid to 5.1 $\mu$S with 250 mA at 4.5 V.

EXAMPLE 9

In this example, the anion suppressor of Example 7 was constructed with platinum plated titanium anode and cathode, anode formed with spaced square openings of 0.020"×0.020", 0.004" apart formed by a chemical etch process followed by platinum plating. It suppressed at 1.0 ml/min 100 mN sodium hydroxide with a background of 2.3 $\mu$S with 300 mA at 3.8 V.

We claim:
1. Apparatus for ion analysis comprising
   (a) an eluent source,
   (b) chromatographic separating means in communication with said eluent reservoir for receiving eluent therefrom, said chromatographic separating means comprising a chromatographic separating medium adapted to separate ionic species of a sample eluted therethrough using eluent solution comprising an electrolyte including transmembrane electrolyte ions of opposite charge to said ionic species,
   (c) suppressor means for treating effluent eluted from said chromatographic separating means, said suppressor means including
      (1) at least one chromatography effluent compartment means having an inlet end and an outlet end,
      (2) at least one detector effluent compartment means having an inlet end and an outlet end,
      (3) at least one ion exchange membrane partitioning said chromatography eluent compartment means and detector effluent compartment means and defining therewith a chromatography effluent flow channel and at least one detector effluent flow channel, respectively, said ion exchange membrane being preferentially permeable to ions of one charge only, positive or negative, of the same charge as said transmembrane electrolyte ions, and including exchangeable ions of said one charge,
      (d) detector means suitable for detecting separated ionic species having an inlet end and an outlet end, said detector means inlet end communicating with said chromatography effluent compartment means outlet end to receive treated chromatography effluent therefrom, and said detector means outlet end communicating with said detector effluent compartment means inlet end to permit flow of post-detection treated effluent thereto, and
      (e) first and second electrode means in electrical communication with said chromatography effluent flow channel and said one detector effluent flow channel, respectively.
2. The apparatus of claim 1 in which said ion exchange membrane is in the form of a flat sheet and said first electrode means is an electrode extending along and flush against the ion exchange membrane, said flat electrode defining spaced openings for contact of solution in said chromatography effluent flow channel with the adjacent ion exchange membrane.
3. The apparatus of claim 1 in which said suppressor means further comprises
   (4) flow-through ion exchange means disposed in said one detector effluent compartment means and having ion exchange sites with exchangeable ions of the same charge as the exchangeable ions of said one ion exchange membrane.
4. The apparatus of claim 1 in which said suppressor means further comprises
   (4) flow-through ion exchange means disposed in said chromatography effluent compartment means and having ion exchange sites with exchangeable ions of the same charge as the exchangeable ions of said one ion exchange membrane.
5. The apparatus of claims 3 or 4 in which said ion exchange means comprises a screen.
6. The apparatus of claims 3 or 4 in which said ion exchange means comprises ion exchange particles.
7. The apparatus of claims 1, 3 or 4 in which said ion exchange membrane is in the form of a cylinder and the detector effluent and chromatographic effluent flow channels are either of circular or annular cross-section.
8. The apparatus of claim 1 in which said suppressor means further comprises
   (4) a second ion exchange membrane of the same type and charge as said one ion exchange membrane, said one ion exchange membrane and second ion exchange membrane defining therebetween said chromatography effluent flow channel, and
   (5) a second detector effluent compartment means, including a wall opposed to and extending coextensively with said second ion exchange membrane and defining therewith a second detector effluent flow channel disposed on the opposite side of said ion exchange membrane from said chromatography effluent flow channel, said first electrode means being disposed in said one detector effluent flow channel and said second electrode being disposed in said second detector effluent flow channel.

* * * * *